(12) United States Patent
Brown et al.

(10) Patent No.: US 10,966,988 B2
(45) Date of Patent: Apr. 6, 2021

(54) METHOD FOR SMOKING CESSATION

(71) Applicant: CALISTA CAPITAL, LLC, New York, NY (US)

(72) Inventors: Karen Glassman Brown, New York, NY (US); Yasmin Aga Khan, Park City, UT (US)

(73) Assignee: CALISTA CAPITAL, LLC, New York, NY (US)

( * ) Notice: Subject to any disclaimer, the term of this patent is extended or adjusted under 35 U.S.C. 154(b) by 66 days.

(21) Appl. No.: 16/486,762

(22) PCT Filed: Sep. 11, 2018

(86) PCT No.: PCT/US2018/050404
§ 371 (c)(1),
(2) Date: Aug. 16, 2019

(87) PCT Pub. No.: WO2019/060171
PCT Pub. Date: Mar. 28, 2019

(65) Prior Publication Data
US 2020/0383992 A1 Dec. 10, 2020

Related U.S. Application Data

(60) Provisional application No. 62/560,959, filed on Sep. 20, 2017.

(51) Int. Cl.
*A61K 31/546* (2006.01)
*A61K 9/00* (2006.01)
(Continued)

(52) U.S. Cl.
CPC .......... *A61K 31/546* (2013.01); *A61K 9/0053* (2013.01); *A61K 9/08* (2013.01); *A61K 9/48* (2013.01)

(58) Field of Classification Search
CPC .. A61K 2300/00; A61K 31/485; A61K 45/06; A61K 9/2031; A61K 31/734; A61K 31/192; A61K 9/2054; A61K 9/0007; A61K 9/2013; A61K 9/0053; A61K 9/0056; A61K 31/465; A61K 9/2072; A61K 9/006; A61K 31/167; A61K 31/4045; A61K 31/55; A61K 31/593; A61K 31/616; A61K 33/06; A61K 9/2027; A61K 9/4808; A61K 31/085; A61K 31/327; A61K 31/46; A61K 31/4709; A61K 31/4745; A61K 31/496; A61K 31/506; A61K 31/555; A61K 31/60; A61K 36/185; A61K 9/0002; A61K 9/0095; A61K 9/2018; A61K 9/205; A61K 9/28; A61K 31/375; A61K 36/81; A61K 47/10; A61K 9/1617; A61K 9/2009; A61K 9/48; A61K 9/50; A61K 9/7007; A61K 47/26; A61K 9/0014; A61K 9/06; A61K 9/1635; A61K 9/1641; A61K 9/1676; A61K 9/20; A61K 9/2095; A61K 9/2806; A61K 9/2893; A61K 2800/58; A61K 2800/622; A61K 31/055; A61K 31/12; A61K 31/122; A61K 31/352; A61K 31/439; A61K 31/4545; A61K 31/522; A61K 33/00; A61K 47/24; A61K 47/34; A61K 47/42; A61K 47/46; A61K 47/60; A61K 8/0241; A61K 8/11; A61K 8/27; A61K 8/29; A61K 8/31; A61K 8/347; A61K 8/361; A61K 8/368; A61K 8/375; A61K 8/466; A61K 8/49; A61K 8/4933; A61K 9/0058; A61K 9/007; A61K 9/08; A61K 9/122; A61K 9/1652; A61K 9/2004; A61K 9/2077; A61K 9/4816; A61K 9/4825; A61K 9/4858; A61K 9/5015; A61K 9/5036; A61K 9/5052; A61K 9/5123; A61K 2800/48; A61K 31/05; A61K 31/4166; A61K 31/565; A61K 31/568; A61K 31/722; A61K 38/26; A61K 47/02; A61K 47/14; A61K 47/32; A61K 47/44; A61K 47/549; A61K 47/585; A61K 47/61; A61K 47/6953; A61K 8/042; A61K 9/0004; A61K 9/0043; A61K 9/1075; A61K 9/145; A61K 9/1611; A61K 9/209; A61K 9/282; A61K 9/2866; A61K 9/4866; A61K 31/546; A01N 59/16; A01N 43/40; A01N 25/34; A01N 25/12;
(Continued)

(56) References Cited

U.S. PATENT DOCUMENTS

| 2005/0131079 | A1* | 6/2005 | Pujara | A61K 9/0095 514/777 |
| 2008/0207601 | A1* | 8/2008 | Sabnani | A61P 25/22 514/221 |

(Continued)

OTHER PUBLICATIONS

International Search Report and Written Opinion for PCT/US2018/050404 dated Dec. 13, 2019 enclosed herewith (12 pages).
(Continued)

*Primary Examiner* — Audrea B Coniglio
(74) *Attorney, Agent, or Firm* — Fitch, Even, Tabin & Flannery, LLP

(57) ABSTRACT

A method of treating a subject for smoking cessation including periodically administering to the subject a pharmaceutically effective amount of cefdinir to treat the subject. Cefdinir for use in treating a subject for smoking cessation. A pharmaceutical composition including a pharmaceutically effective amount of cefdinir for use in treating a subject for smoking cessation.

16 Claims, No Drawings

(51) Int. Cl.
*A61K 9/08* (2006.01)
*A61K 9/48* (2006.01)

(58) Field of Classification Search
CPC ......... A01N 37/06; A01N 57/12; A61P 25/36;
A61P 25/04; A61P 29/00; A61P 43/00;
A61P 1/16; A61P 25/30; A61P 17/02;
A61P 25/34; A61P 3/04; A61P 3/10
See application file for complete search history.

(56) References Cited

U.S. PATENT DOCUMENTS

2008/0287673 A1* 11/2008 Parthasaradhi Reddy ..................
C07D 501/00
540/220
2014/0166028 A1   6/2014 Fuisz et al.

OTHER PUBLICATIONS

Alajaji c t al. "Effects of the beta-lactarn antibiotic ceftriaxone on nicotine withdrawal and nicotine-induced reinstatement of preference in mice", Psychopharmacology (Berl). 2013. vol. 228(3), 14 pgs, entire document, especially: abstract.
Philogene-Khalid et al. "Effects of ceftriaxone on conditioned nicotine reward in rats", Behav Pharmacol. Sep. 2017. vol. 28(6), pp. 485-488, entire document, especially: abstract.

* cited by examiner

METHOD FOR SMOKING CESSATION

CROSS-REFERENCE TO RELATED APPLICATIONS

The present application is a U.S. national phase application filed under 35 U.S.C. § 371 of International Application No. PCT/US2018/050404, filed Sep. 11, 2018, which claims priority to U.S. provisional application Ser. No. 62/560,959, filed Sep. 20, 2017, the disclosure of each of which is incorporated herein by reference in its entirety.

TECHNICAL FIELD

The present invention relates to methods for smoking cessation by administration of a pharmaceutically effective amount of cefdinir.

BACKGROUND OF THE INVENTION

Tobacco use causes nearly 6 million deaths per year globally, with current trends showing that tobacco use will cause more than 8 million deaths annually by 2030. In the United States alone, cigarette smoking is responsible for more than 480,000 deaths per year, including more than 41,000 deaths resulting from secondhand smoke exposure. The economic cost of smoking for the United States is more than $300 billion each year, including nearly $170 billion in direct medical care for adults and more than $156 billion in lost productivity due to premature death and exposure to secondhand smoke.

At the present time, existing products for assisting in smoking cessation include nicotine-replacement products, which may take the form of a patch, gum, nasal spray, inhaler, or lozenge. Success rates relating to these products have been found to be as low as 15% after one year. Moreover, there are non-nicotine-based prescription medications on the market, such as varenicline (under the trade name of CHANTIX) and bupropion (under the trade name of ZYBAN). These medications have similarly low success rates, with CHANTIX being found in clinical trials as having only a 14% success rate after six months, while simultaneously resulting in tens of thousands of patient adverse reactions being reported to the Food and Drug Administration (FDA). Therefore, there is a need for effective and safe means for smoking cessation.

SUMMARY OF THE INVENTION

This invention provides a method of treating a subject for smoking cessation including periodically administering to the subject a pharmaceutically effective amount of cefdinir to treat the subject.

Implementations of the invention may include one or more of the following features. The pharmaceutically effective amount of cefdinir may be effective to reduce a clinical sign or symptom associated with tobacco addiction or smoking addiction in the subject, and/or a tobacco-induced health issue or a smoking-induced health issue in the subject. The periodic administration may be effected orally, and cefdinir may be administered in capsule form or oral suspension form. An amount of cefdinir administered may be in a range of 125-600 mg per dose, including 125 mg per dose, 250 mg per dose, 300 mg per dose, or 600 mg per dose. The periodic administration may be a once-daily administration or a twice-daily administration. The periodic administration may continue for at least 5 days or for at least 10 days. The subject may be human.

This invention also provides cefdinir for use in treating a subject for smoking cessation.

This invention further provides a pharmaceutical composition including a pharmaceutically effective amount of cefdinir for use in treating a subject for smoking cessation.

DETAILED DESCRIPTION OF THE INVENTION

This invention provides a method of treating a subject for smoking cessation including periodically administering to the subject a pharmaceutically effective amount of cefdinir to treat the subject.

In one embodiment, the pharmaceutically effective amount of cefdinir is effective to reduce a clinical sign or symptom associated with tobacco or smoking addiction and/or tobacco- or smoking-induced health issues in the subject.

In one embodiment, the periodic administration of cefdinir is effected orally. In one embodiment, cefdinir is administered in capsule form. In another embodiment, cefdinir is administered in oral suspension form.

In one embodiment, the amount of cefdinir administered is 125-600 mg per dose. In another embodiment, the amount of cefdinir administered is 125 mg per dose. In another embodiment, the amount of cefdinir administered is 250 mg per dose. In another embodiment, the amount of cefdinir administered is 300 mg per dose. In another embodiment, the amount of cefdinir administered is 600 mg per dose.

In one embodiment, a dose or dosage of cefdinir is administered to the subject once per day. In another embodiment, a dose or dosage of cefdinir is administered to the subject twice per day.

In one embodiment, the periodic administration continues for at least 5 days. In one embodiment, the periodic administration continues for 5 days. In another embodiment, the periodic administration continues for 10 days.

In one embodiment, the subject is human.

This invention also provides cefdinir for use in treating a subject for smoking cessation.

This invention further provides a pharmaceutical composition including a pharmaceutically effective amount of cefdinir for use in treating a subject for smoking cessation.

For the foregoing embodiments, each embodiment disclosed herein is contemplated as being applicable to each of the other disclosed embodiments.

Disclosed is a method of treating a subject for smoking cessation using cefdinir. Cefdinir is a third-generation oral cephalosporin antibiotic commonly sold under the trade names of CEFZON or OMNICEF. It has been previously understood that cefdinir may be used to treat various types of bacterial infections, such as bronchitis (infection of the airway tubes leading to the lungs), pneumonia, and infections of the skin, ears, sinuses, throat, and tonsils. The effects of cefdinir on smoking cessation have not been reported. As described herein, administration of cefdinir is effective to treat a subject for smoking cessation.

Administration of cefdinir is advantageous over existing treatments for smoking cessation because cefdinir can be administered orally and has well-documented success in terms of safe administration with minor side effects.

As used herein, and unless stated otherwise, each of the following terms shall have the definition set forth below.

As used herein, an "amount," "dose," or "dosage" of cefdinir as measured in milligrams refers to the milligrams of cefdinir present in a preparation, regardless of the form of the preparation. Therefore, a "dose of 125 mg cefdinir" means the amount of cefdinir in a preparation is 125 mg, regardless of the form of the preparation.

As used herein, "a subject" generally means a subject who is attempting to quit smoking or using tobacco-based products, such as cigarettes.

As used herein, "effective" or "pharmaceutically effective" when referring to an amount of cefdinir refers to the quantity of cefdinir that is sufficient to yield a desired therapeutic response without undue adverse side effects (such as toxicity, irritation, or allergic response) commensurate with a reasonable benefit/risk ratio when used in the manner of this invention.

As used herein, "treating" encompasses, e.g., inducing inhibition, regression, or stasis of a disorder, or lessening, suppressing, inhibiting, reducing the severity of, eliminating, or ameliorating a symptom of the disorder, where the disorder includes tobacco or smoking addiction, tobacco- or smoking-induced health issues, and the like.

In an embodiment of the present invention, a subject is administered a pharmaceutically effective amount of cefdinir at several times during a treatment regimen. At the conclusion of this treatment regiment, the subject feels no desire or, at a minimum, a decreased desire to smoke or otherwise use tobacco-based products, such as cigarettes.

Table 1 illustrates cefdinir plasma concentrations and pharmacokinetic parameter values following administration of single 300 and 600 mg oral doses of cefdinir to adult subjects.

TABLE 1

Mean (±SD) Plasma Cefdinir Pharmacokinetic Parameter Values Following Administration of Capsules to Adult Subjects

| Dose | Cmax (µg/mL) | tmax (hr) | AUC (µg · hr/mL) |
|---|---|---|---|
| 300 mg | 1.60 (0.55) | 2.9 (0.89) | 7.05 (2.17) |
| 600 mg | 2.87 (1.01) | 3.0 (0.66) | 11.1 (3.87) |

The embodiments and examples above are illustrative, and many variations can be introduced to them without departing from the spirit of the disclosure or from the scope of the appended claims. For example, elements and/or features of different illustrative and exemplary embodiments herein may be combined with each other and/or substituted with each other within the scope of this disclosure. The objects of the invention, along with various features of novelty which characterize the invention, are pointed out with particularity in the claims annexed hereto and forming a part of this disclosure.

What is claimed is:

1. A method of treating a subject for smoking cessation comprising periodically administering to the subject a pharmaceutically effective amount of cefdinir to treat the subject.

2. The method of claim 1, wherein the pharmaceutically effective amount of cefdinir is effective to reduce a clinical sign or symptom associated with tobacco addiction or smoking addiction in the subject.

3. The method of claim 1, wherein the pharmaceutically effective amount of cefdinir is effective to reduce a clinical sign or symptom associated with a tobacco-induced health issue or a smoking-induced health issue in the subject.

4. The method of claim 1, wherein the periodic administration is effected orally.

5. The method of claim 4, wherein cefdinir is administered in capsule form.

6. The method of claim 4, wherein cefdinir is administered in oral suspension form.

7. The method of claim 1, wherein an amount of cefdinir administered is in a range of 125-600 mg per dose.

8. The method of claim 7, wherein the amount of cefdinir administered is 125 mg per dose.

9. The method of claim 7, wherein the amount of cefdinir administered is 250 mg per dose.

10. The method of claim 7, wherein the amount of cefdinir administered is 300 mg per dose.

11. The method of claim 7, wherein the amount of cefdinir administered is 600 mg per dose.

12. The method of claim 1, wherein the periodic administration is a once-daily administration.

13. The method of claim 1, wherein the periodic administration is a twice-daily administration.

14. The method of claim 1, wherein the periodic administration continues for at least 5 days.

15. The method of claim 1, wherein the periodic administration continues for at least 10 days.

16. The method of claim 1, wherein the subject is human.

* * * * *